United States Patent [19]
Sweeney et al.

[11] Patent Number: 5,533,980
[45] Date of Patent: Jul. 9, 1996

[54] PROTECTIVE CAP ASSEMBLY FOR A MEDICAL DEVICE PASSAGEWAY

[75] Inventors: Niall Sweeney, Rutherford; Richard J. Caizza, Barry Lakes, both of N.J.; Marian H. Gravel, Highland, N.Y.; Bronwen L. Walters, Lyndhurst, N.J.

[73] Assignee: Becton, Dickinson and Company, Franklin Lakes, N.J.

[21] Appl. No.: 298,248

[22] Filed: Aug. 30, 1994

[51] Int. Cl.$^6$ ..................................................... A61M 5/32
[52] U.S. Cl. ........................... 604/192; 604/263; 604/110
[58] Field of Search ..................................... 220/254, 337, 220/339, 352, 331, 353, 252; 604/187, 238, 263, 403, 207, 192, 110

[56] References Cited

U.S. PATENT DOCUMENTS

4,842,587  6/1989  Poncy ...................... 604/198
5,015,234  5/1991  Jullien ...................... 604/110

*Primary Examiner*—Corrine M. McDermott
*Assistant Examiner*—N. Kent Gring
*Attorney, Agent, or Firm*—V. A. Castiglione

[57] ABSTRACT

A protective safety cap assembly for the passageway of a medical device is provided. The safety cap assembly includes a cap that is guided for sliding and pivotable movement between a closed position where the proximal end of the medical device is easily accessed and a closed position where the proximal end of the medical device is sealed. The medical devices which can be protected by the cap assembly include hypodermic syringes, stopcock assemblies associated with I.V. lines and catheters, or the like. A medical worker holding the medical device in one hand can easily and repeatedly move the cap between the opened and closed position with a thumb or forefinger of the hand holding the medical device.

28 Claims, 12 Drawing Sheets

PROTECTIVE CAP ASSEMBLY FOR A MEDICAL DEVICE PASSAGEWAY

FIELD OF THE INVENTION

The subject invention relates to a protective cap assembly for selectively sealing and unsealing a passageway in a medical device and, in particular, to a protective cap assembly for selectively sealing and unsealing the passageway in an end of a hypodermic syringe barrel.

DESCRIPTION OF THE PRIOR ART

The prior art hypodermic syringe includes an elongate barrel having an open proximal end, a distal end and a fluid receiving chamber therebetween. The distal end of the prior art syringe barrel includes a tip with a passageway extending into communication with the chamber of the barrel. The distal end also is configured to releasably engage a needle cannula, such that the needle cannula communicates with the passageway through the tip of the syringe barrel. A plunger is inserted into the open proximal end of the barrel. Movement of the plunger toward the distal end of the barrel urges fluid out of the chamber and through the passageway. Movement of the plunger away from the distal end of the syringe barrel draws fluid through the passageway and into the chamber.

Hypodermic syringes often are filled at a location in a health care facility remote from the patient, such as an in-hospital pharmacy. The filled syringes are then transported to locations where the drug is administered. While the syringe may be shipped with the needle cannula, as a safety measure the syringes are normally transported without a needle cannula. This procedure reduces the risk of accidental needle sticks, reduces storage space and allows the health care worker to select the most appropriate means for administering the drug (e.g., metallic needle cannula, blunt cannula or IV fitting). The tip of the prior art syringe barrel should be sealed or at least covered between the time the syringe is filled and the time the drug is administered. This sealing is necessary to avoid leakage from the syringe, the ingress of foreign matter and air into the syringe, and, in general, the contamination of the drug.

Some medical procedures require a drug to be administered in small doses over a period of time. For example, an initial dose of anesthesia may be administered preoperatively. The anesthesiologist may then administer smaller doses of anesthesia intra-operatively to keep the patient stabilized. The hypodermic syringe may not require a needle cannula for these procedures, and the anesthesiologist may merely place the tip of the syringe barrel directly into communication with a fitting on an intravenous line. Between successive administrations of anesthesia, the syringe may be deposited on a surgical table near the patient. The passageway through the distal end of the syringe barrel should be sealed or covered between successive administrations of anesthesia to avoid leakage and contamination.

Prior art hypodermic syringes also are used to draw fluid from a patient for analysis. These bodily fluids typically are accessed with a sharply pointed metallic needle cannula. However, for the reasons explained above, it is oftentimes desirable to separate the needle cannula from the hypodermic syringe before sending the filled syringe to the laboratory. Once again, it is necessary to seal or cover the tip during transportation to prevent leakage and to avoid contamination.

In still other situations, a prior art hypodermic syringe may be used to flush lines of medical equipment. For example, the hypodermic syringe may be placed in communication with a dialysis machine and fluids may be drawn therefrom. These fluids may be contaminated, and hence it is again desirable to seal the hypodermic syringe to prevent leakage.

The prior art hypodermic syringe typically is sealed or covered with a separate cap that can be telescoped over the distal end of the syringe barrel. These separate caps function well, but are easily lost. Separate caps also create inventory control and disposal problems. Furthermore, the inconvenience of having to find and manipulate a separate cap may encourage health care workers to simply disregard the cap or to use it improperly.

Some prior art hypodermic syringes tether a cap to the syringe barrel with an elongate flexible strap. The health care worker must manipulate the cap, the strap and the hypodermic syringe to place the cap on the barrel or to remove the cap therefrom. This manipulation can be cumbersome and requires the health care worker to use both hands for sealing or unsealing the hypodermic syringe. Unfortunately, exigencies of a health care facility often prevent the health care worker from having two free hands for capping a hypodermic syringe. Thus, the health care worker may, at least temporarily, leave the hypodermic syringe unsealed. The tethered cap also may visually or physically interfere with the prior art hypodermic syringe.

Co-pending patent application Ser. No. 07/950,113 is assigned to the assignee of the subject invention and discloses a single handedly actuatable protective cap for a hypodermic syringe. The cap is hinged near the distal end of the syringe barrel and rotates 180° for selectively opening or sealing the passageway through the tip of the barrel. Although the cap shown in co-pending application Ser. No. 07/950,113 is convenient to open or close, the opened cap can visually or physically interfere with proper use of the hypodermic syringe. For example, the cap may complicate attempts to connect the hypodermic syringe to a fitting of an intravenous line.

SUMMARY OF THE INVENTION

The subject invention is directed to a cap assembly for selectively sealing the passageway through the tip at the distal end of a medical device.

For purposes of illustration and not of limitation, the assembly is herein described primarily with reference to its use with medical syringes. However, it will be understood and realized that the advantages and features of the cap assembly herein described are not strictly limited to sealing medical syringes and that the device may be readily accommodated to sealing passageways of any medical device. For instance, the relative dimensions of the various assembly components and, in particular, the collar configuration of the cap assembly may be designed and/or otherwise adapted to accommodate any number of medical devices having a luer collar, so that the passageways of those medical devices can be sealed or unsealed. For example, the collar configuration may be provided with a thread to permit attachment to a female luer-lock stopcock associated with, for instance, intravenous lines, catheters or the like. The cap assembly can then be used to selectively seal the stopcock when not in use so as to preserve sterility of the line. Other applications and uses of the cap assembly will be realized by those skilled in the art.

The cap assembly includes at least one wall near the tip of the syringe barrel and a cap slidably engaged with the wall. The wall and the cap are configured for permitting slidable movement of the cap between a first position where the passageway through the tip of the syringe barrel is open, and a second position where the passageway is sealed by the cap. The wall may define a channel with a proximal portion extending generally parallel to the tip of the syringe barrel, with the channel defining a distal portion angularly aligned to the tip, and the cap may be slidably engaged in the channel. In this regard, the wall defining the channel may include guide walls at the interface between the proximal and distal portions of the channel for positively guiding the cap between the first or open position and the second or closed position.

The wall with the channel may be unitary with the syringe barrel. For example, the channel may be unitarily formed as part of the luer collar at the distal end of the syringe barrel. Alternatively, the wall with the channel may be part of a collar that is lockingly engaged over the distal end of the syringe barrel. For example, the collar may be lockingly engaged over the luer collar of a prior art hypodermic syringe barrel.

The cap can be translated and rotated between the first position where the cap is adjacent and parallel to the luer collar or barrel and the second position where the cap sealingly engages the tip of the syringe barrel. An actuator tab may extend from the cap and may be dimensioned for convenient actuation by the thumb or forefinger of a user.

As explained further herein, the cap can be moved conveniently and repeatedly between the opened and closed positions by a finger of the hand in which a syringe barrel is held. The cap is never separated from the syringe barrel, and hence cannot be lost or misplaced. The one handed opening and closing enables the health care worker to attend to other responsibilities while conveniently and easily sealing or unsealing the syringe barrel.

BRIEF DESCRIPTION OF THE DRAWINGS

FIG. 15 illustrates a stopcock assembly having a female luer fitting associated with medical devices, such as IV lines, catheters, or the like.

DETAILED DESCRIPTION OF THE PREFERRED EMBODIMENT

Figure 1:
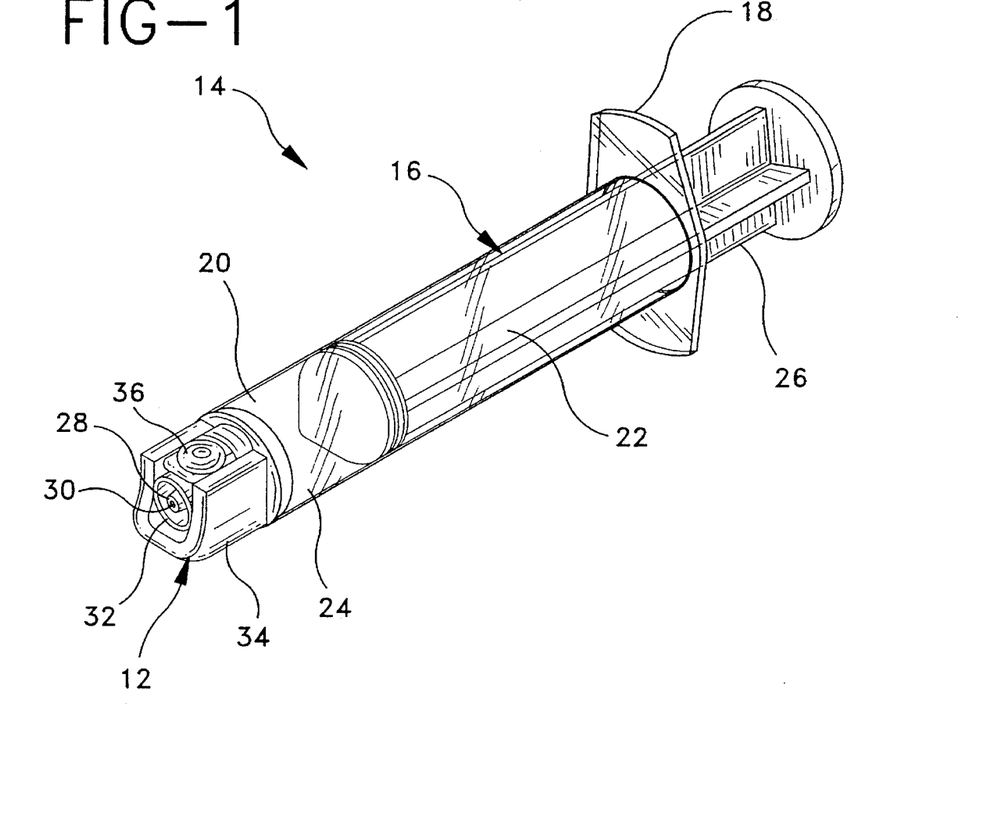
FIG. 1 is a perspective view of a hypodermic syringe with the roll cap assembly of the subject invention mounted thereto and shown in an open condition.
Figure 2:
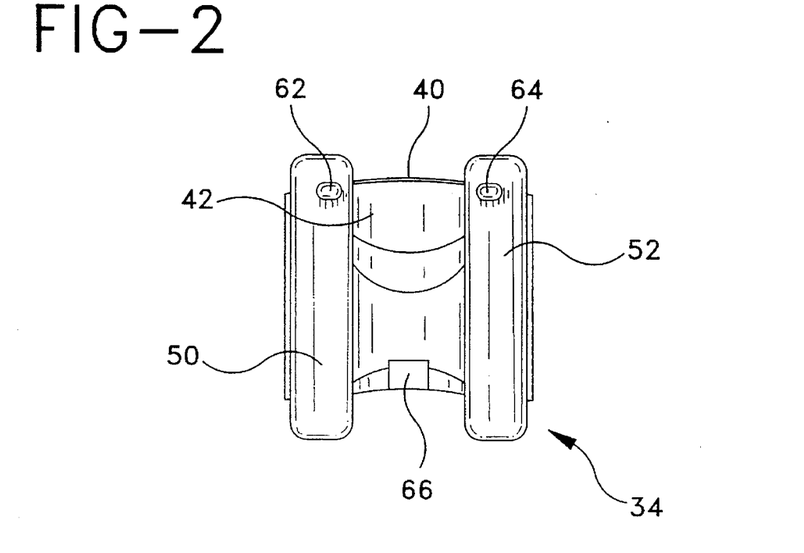
FIG. 2 is a front elevational view of the collar for the cap assembly shown in FIG. 1.
Figure 3:
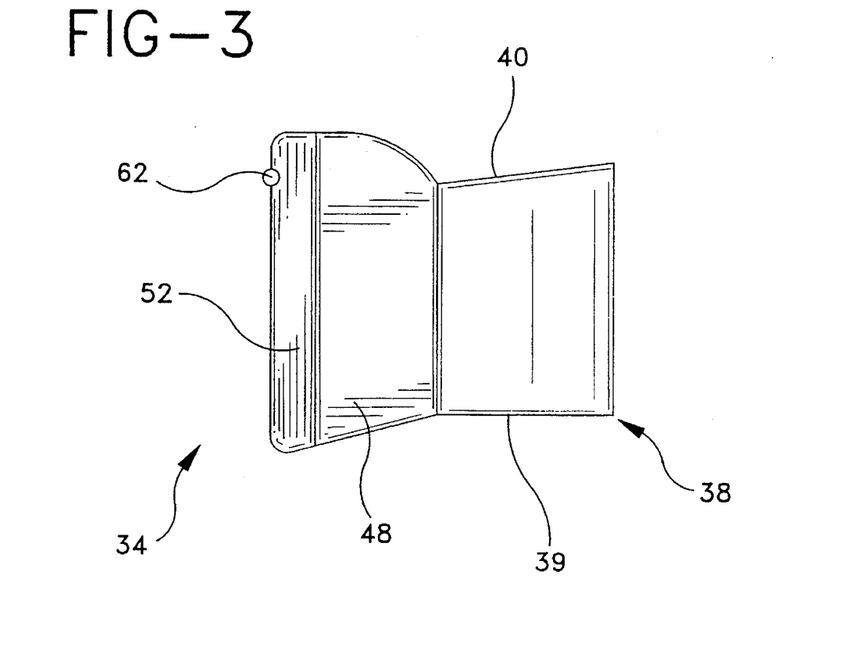
FIG. 3 is a side elevational view of the collar.

Turning now to the drawings, wherein like numerals denote like components, a protective cap assembly in accordance with the subject invention is identified generally by the numeral 12 in FIGS. 1 and 11–14. Protective cap assembly 12 is used with a hypodermic syringe 14 having a syringe barrel 16. As shown in FIG. 1, syringe barrel 16 includes an open proximal end 18, a distal end 20, and a generally cylindrical side wall 22 extending therebetween and defining a fluid receiving chamber 24. A plunger 26 is inserted into chamber 24 of syringe barrel 16 from open proximal end 18. Plunger 26 is dimensioned for sliding fluid tight engagement with cylindrical wall 22 of chamber 24.

Distal end 20 of syringe barrel 16 includes an elongate tip 28 having a passage 30 extending axially therethrough and communicating with chamber 24. A luer collar 32 concentrically surrounds tip 28, and includes an array of internal threads for releasably engaging the hub of a needle cannula. Thus, the lumen through the needle cannula can be placed in communication with passage 30 through tip 28 for delivering fluid from chamber 24 to a patient, or for drawing fluid from a patient into chamber 24.

Protective cap assembly 12 includes a collar 34 and a roll cap 36. As explained in greater detail below, roll cap 36 is engaged in collar 34 for movement between the open position shown in FIG. 1, where passage 30 through tip 28 is open and readily accessible, and the closed position shown in FIGS. 12–14, where passage 30 is safely sealed.

Figure 11:
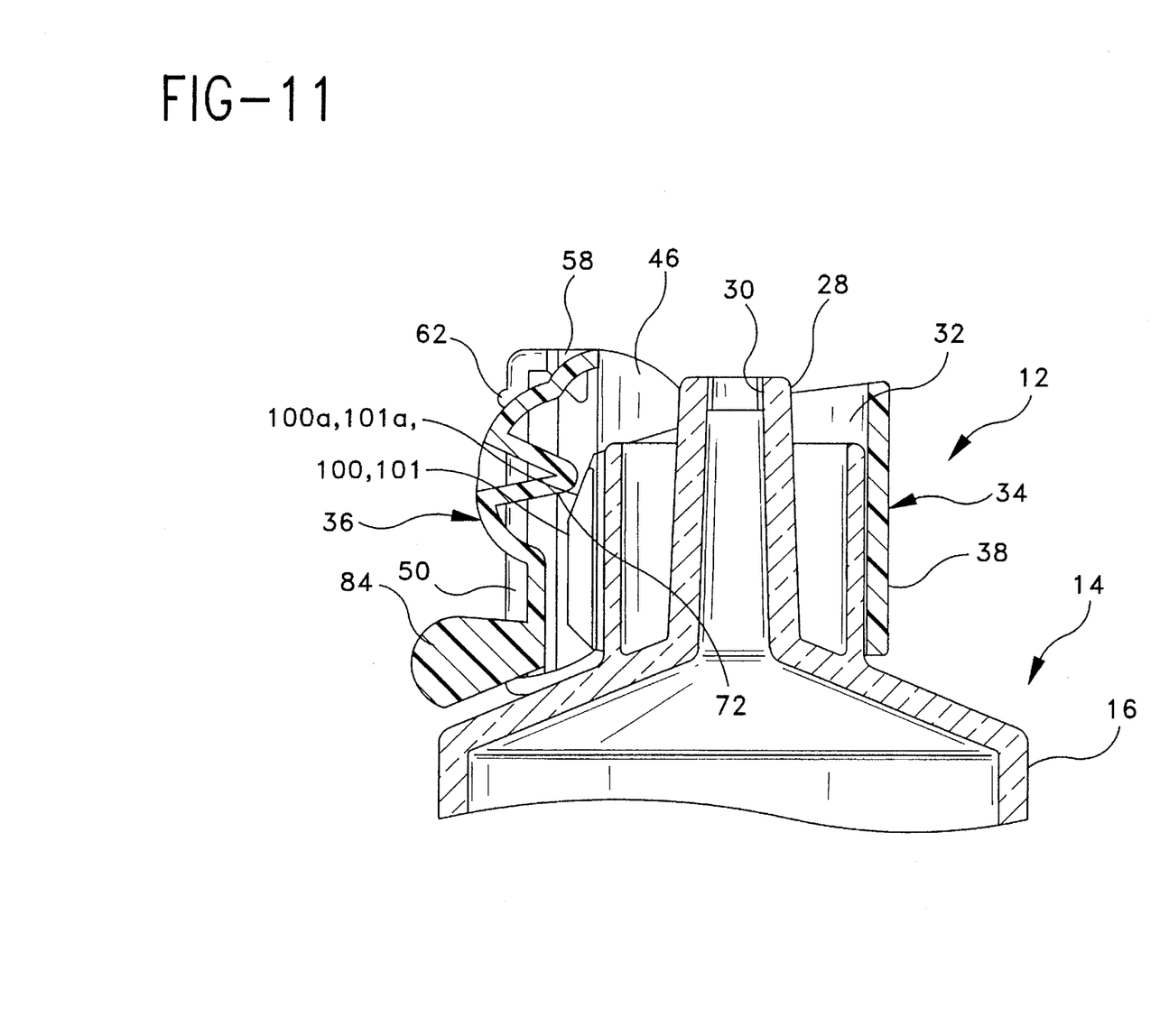
FIG. 11 is a cross-sectional view taken along line 11—11 in FIG. 1.
Figure 12:
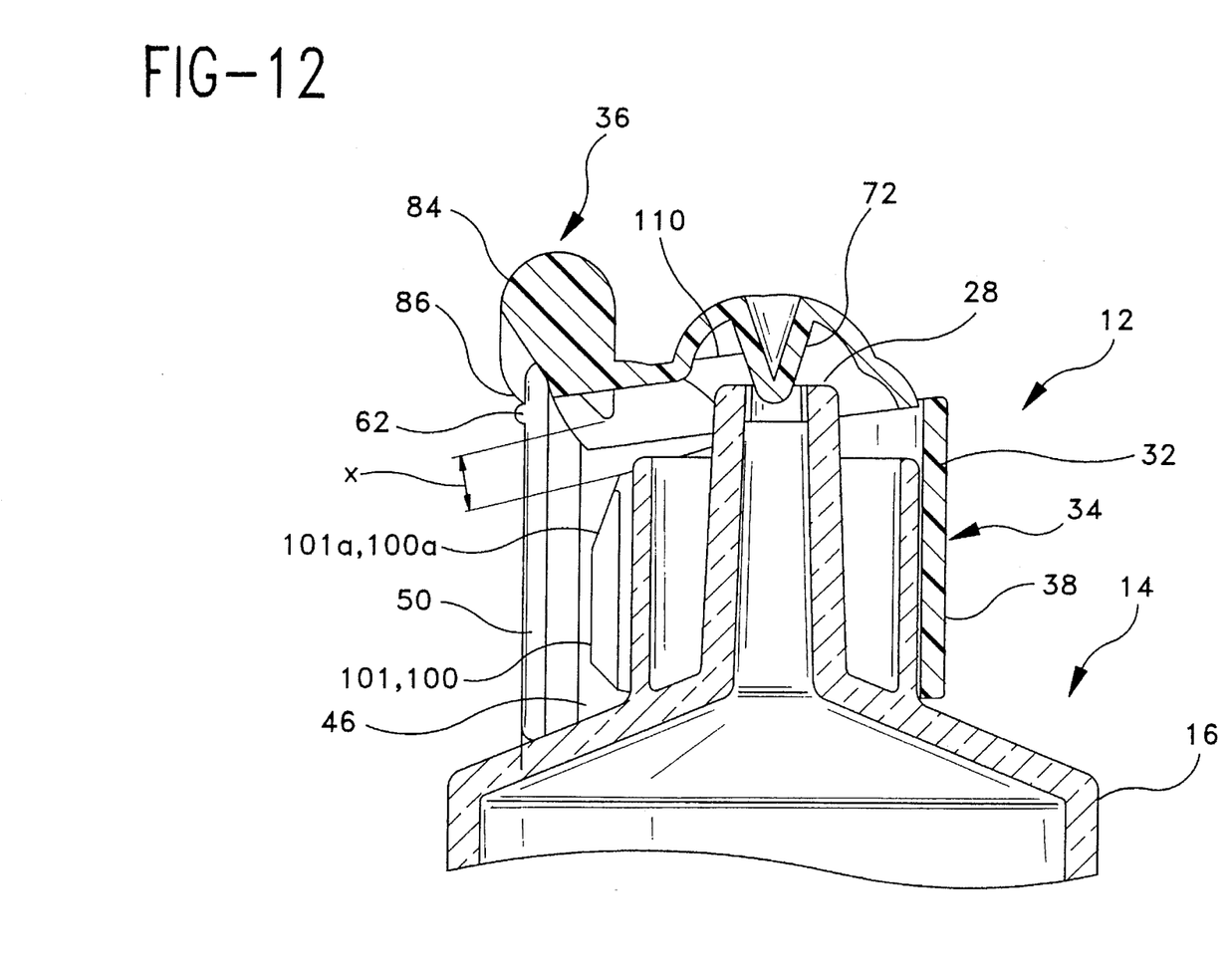
FIG. 12 is a cross-sectional view similar to FIG. 11, but showing the cap in a closed condition.

As shown in FIGS. 2–6, collar 34 may be unitarily molded from a thermoplastic material and includes an axially short tubular mounting portion 38 having opposed proximal and distal ends 39 and 40. Mounting portion 38 may further include an inner circumferential surface 42 defining a diameter "a" which enables collar 34 to be slidably mounted over luer collar 32 of syringe barrel 16. As seen in FIGS. 11 and 12, the mounting portion 38 may also define an axis substantially aligned with the axis of the syringe barrel. Portions of inner circumferential surface 42 of collar 34 adjacent proximal end 39 thereof may define barbs (not shown) projecting inwardly. The barbs may be configured to gradually bite into the thermoplastic material of syringe barrel 16 as collar 34 is slidably advanced in a proximal direction over luer collar 32. The configuration of barbs will substantially prevent removal of collar 34 in a distal direction after it has been securely mounted to luer collar 32.

If, for instance, luer collar 32 were not provided at the distal end of the syringe barrel (as is the case, for example, with luer slip devices such as luer slip syringes), the structure of the collar 34 and/or the inner circumferential surface 42 thereof may the configured to adapt to a luer slip configuration associated, for instance, with luer slip syringes. That is, the device might be configured to engage the elongate luer tip 28. For instance, as seen in FIG. 4C, a washer 150 or similar structure might be incorporated or otherwise formed or disposed at the base of collar 34, with an opening formed therein adapted to frictionally engage the outer surface of elongate tip 28.

As will be explained in further detail below, for certain applications it will be understood and realized by those skilled in the art that it may be advantageous to secure the cap assembly 12 for rotation about the fitting to which the assembly is mounted. For instance, by replacing the barbs on the inner circumferential surface 42 of the collar 34 with one or more circumferential projections 111 disposed about all or a part of the circumference of the surface 42 the cap assembly 12 can be attached to the luer collar 32 in a manner to permit rotation of the cap assembly respective to the luer collar. See FIGS. 4A and 4B. The projection(s) 111 can be formed as one or more rings circumferentially disposed on the surface 42; as one or more discontinuous segments of a circumferential ring; as one or more discrete projections of similar or varied shapes circumferentially disposed along a ring; or in various other manners as need or desire dictate. The projection(s) 111 may mate with a corresponding groove or channel (not shown) formed around the circumference of luer collar 32. While projection(s) 111 need not extend about the entire circumference of surface 42, if so disposed, the projection(s) may be arranged around the center of collar 34 to promote stability of the assembly while mounted to the luer collar 32. As collar 34 is proximally advanced over luer collar 32, the projections 111 will deform over the surface of collar 34 and snap into place in the grooves, thereby providing secure engagement of the cap assembly 12 with the luer collar 32 but permitting the assembly 12 to easily rotate about the axis of the fitting. To this extent, it will be realized that a slight clearance may be provided when configuring the projection(s) 111 and the corresponding groove(s) to ensure smooth rotation.

Figure 4:
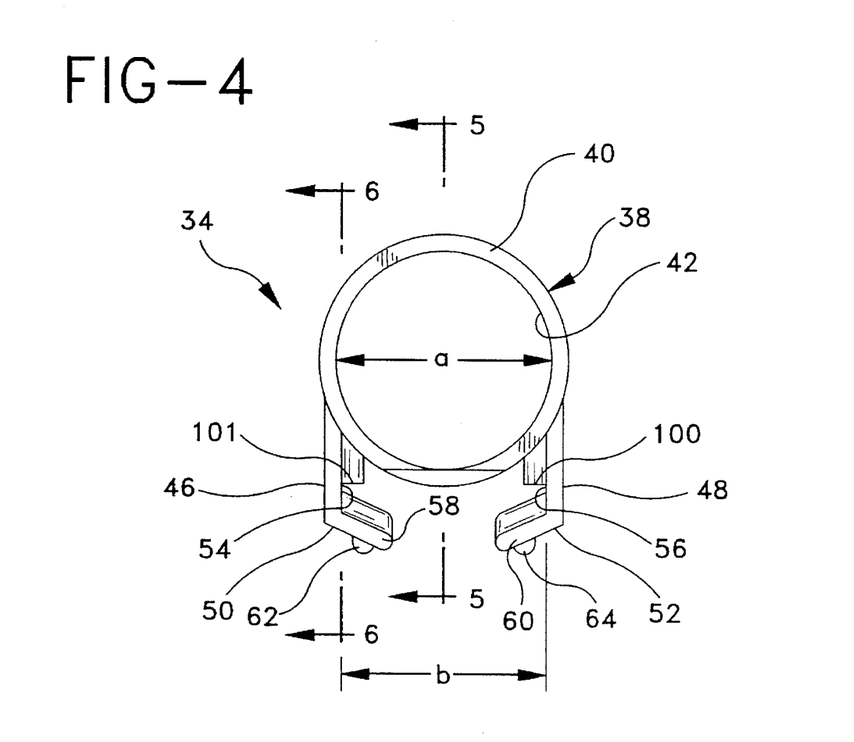
FIG. 4 is a top plan view of the collar.

As best seen in FIG. 4, a pair of parallel side walls 46 and 48 project outwardly from the outer circumferential surface of mounting portion 38 of collar 34. Collar 34 further includes a pair of retaining walls 50 and 52 which project generally toward one another from portions of side walls 46 and 48 remote from mounting portion 38. Side walls 46 and 48 and retaining walls 50 and 52 define channels 54 and 56 which face one another. The distance between the inner surfaces of side walls 46 and 48 define a width "b". The proximal ends of channels 54 and 56 are substantially parallel to the axis of mounting portion 38 of collar 34.

Referring again to FIGS. 4–6, a pair of guide walls 100, 101 are also defined within each of channels 54 and 56, respectively. The guide walls 100 and 101, generally aligned along the axis of mounting portion 38 of collar 34, engage and trap roll cap 36 within the channels 54 and 56 between the guide walls 100, 101 and retaining walls 50, 52, so as to facilitate the movement of the roll cap 36 between its open and closed (sealed) positions. For purposes which will soon be realized, each of the guide walls 100, 101 includes a respective ramped portion 100a, 101a located near the distal end of the collar 34. The ramped portions 100a, 101a are angled toward the axis of the mounting portion 38 at a generally acute angle "θ" (FIG. 5) chosen, for instance, according to the dimensions of surrounding components, so as to facilitate the assembly of roll cap 36 into the collar 34 as well as to assist in the operation of roll cap 36 between its opened and closed (sealed) positions.

Figure 13:
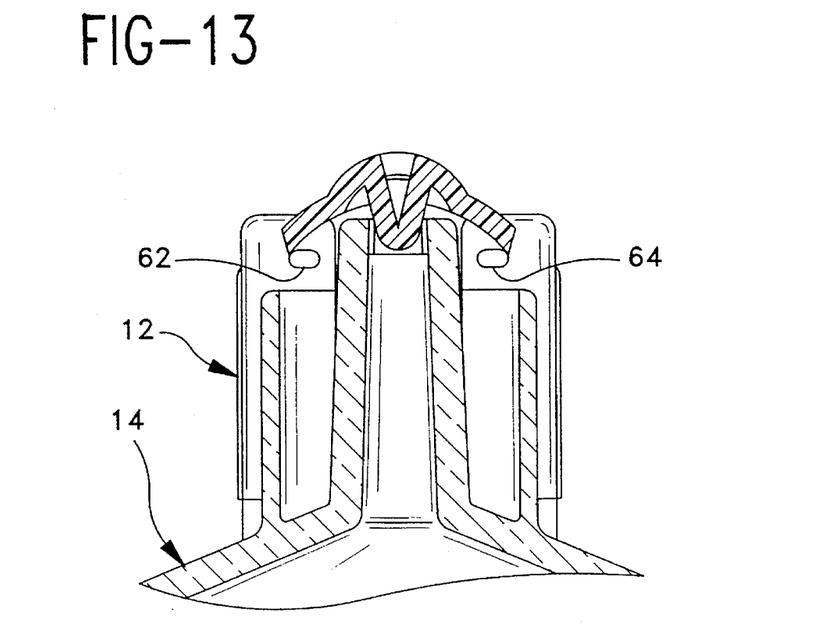
FIG. 13 is a front elevational view of the collar showing the cap in cross-section, in a closed condition, as taken along line 102—102 of FIG. 7.
Figure 14:
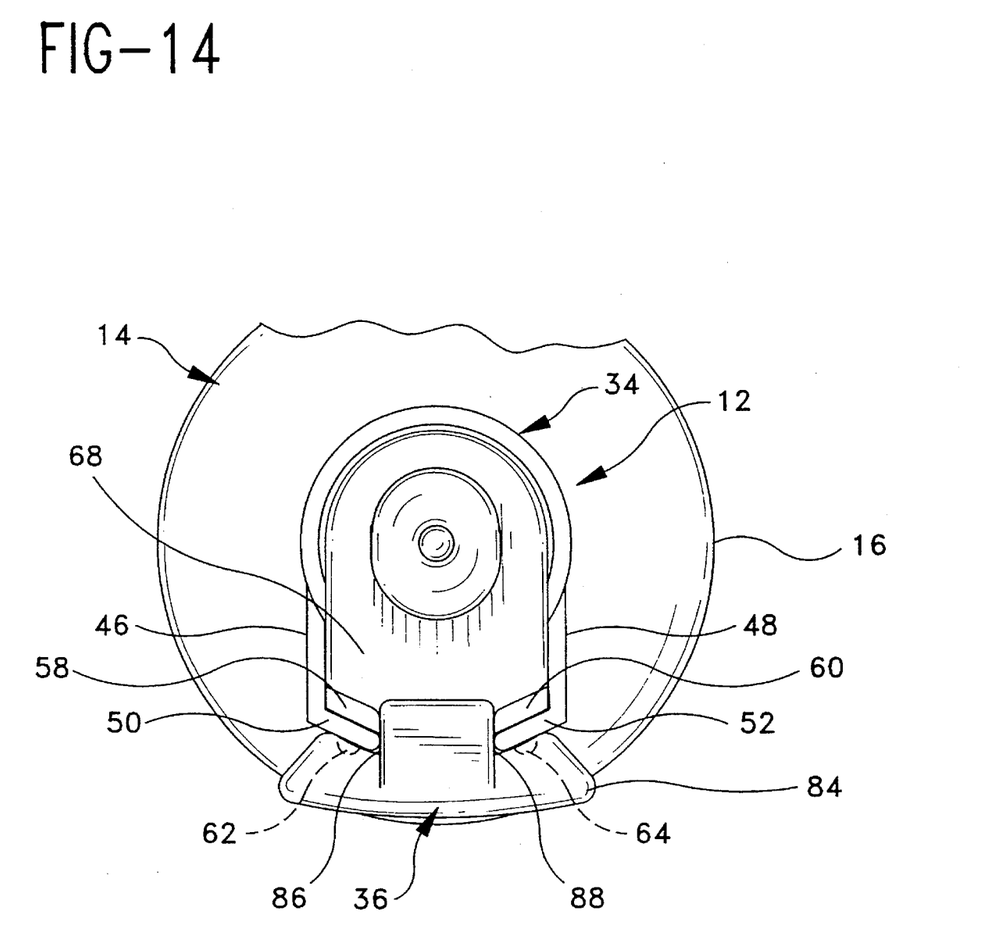
FIG. 14 is a top plan view of the roll cap assembly with the cap in the closed condition.

The portions of side walls 46 and 48 adjacent distal end 40 of collar 34 also include guide projections 58 and 60 which, with the assistance of ramped portions 100a and 101a of the guide walls 100, 101, effectively angle channels 54 and 56 toward the axis of mounting portion 38 for guiding roll cap 36 from the open condition shown in FIG. 1 to the closed position shown in FIGS. 12–14. Projections 58 and 60 also function to hold roll cap 36 in the closed condition as explained further herein.

Retaining walls 50 and 52 are further characterized by locking projections 62 and 64 on sides of retaining walls 50 and 52 projecting outwardly therefrom. As explained further herein, locking projections 62 and 64 cooperate with portions of roll cap 36 for locking roll cap 36 in the closed condition illustrated in FIGS. 12–14.

Figure 10:
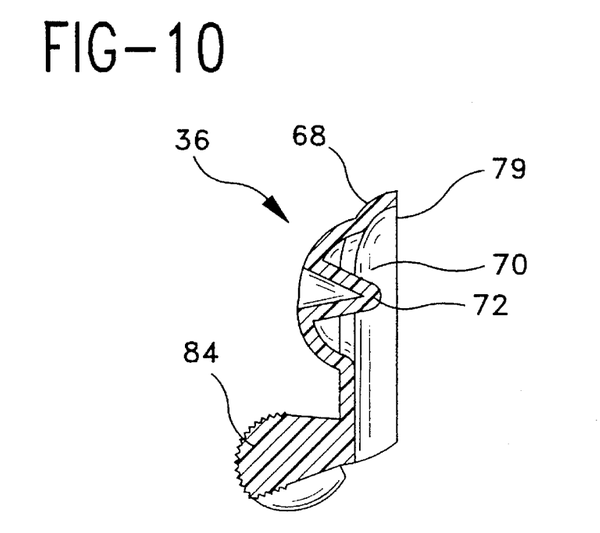
FIG. 10 is a cross-sectional view taken along line 10—10 in FIG. 7.
Figure 12A:
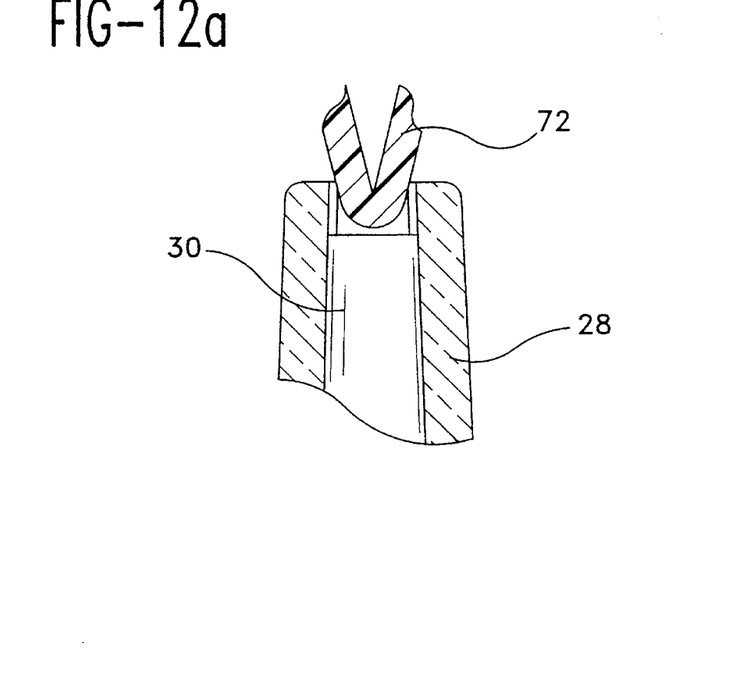
FIG. 12A depicts a manner by which a central projection of the cap seals the syringe tip.
Figure 17:
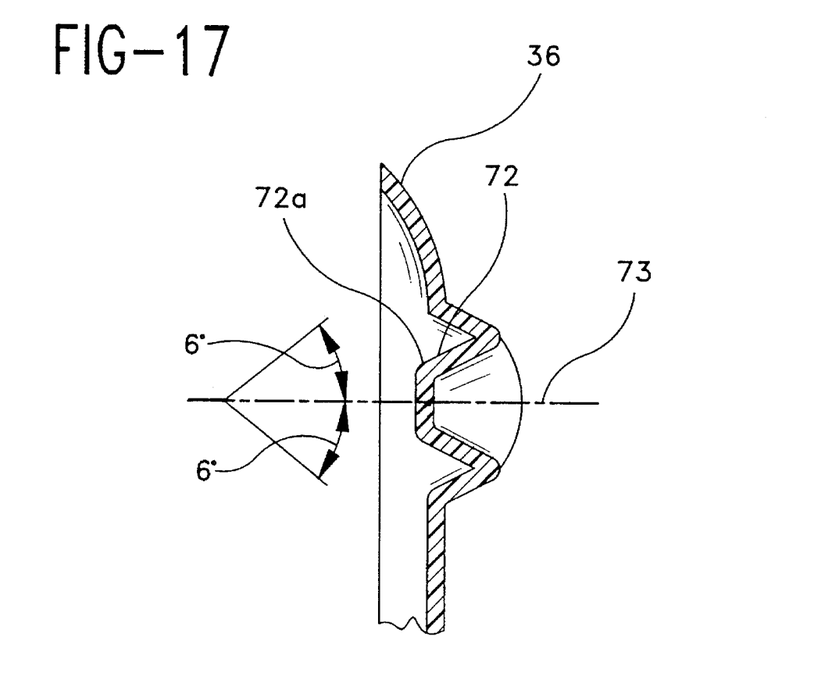
FIG. 17 is a partial cross-sectional view taken along line 16—16 of FIG. 16 illustrating a tapered sealing projection.

Roll cap 36, as illustrated in FIGS. 7–10, may be unitarily molded from a thermoplastic material. More particularly, roll cap 36 includes an outer surface 68 for facing away from syringe 14 and an opposed inner surface 70 for facing toward syringe 14. Inner surface 70 is characterized by a central sealing projection 72 for sealingly engaging portions of tip 28 of syringe 14 in proximity to passage 30. As best seen in FIGS. 10 and 12, sealing projection 72 may be formed in a generally frusto-conical configuration which can conveniently seal the tip 28 of the syringe barrel by blocking passage 30. As depicted in FIG. 17, the frustoconical configuration of sealing projection 72 may define, for instance, a conically tapered wall component 72a inclined, for instance, approximately six degrees from the normal as defined by an axis 73 perpendicular to the cap 36. It will be understood that other acute angles may also be devised as need or desire dictate. The conically tapered shape provided by the frusto-conical configuration of the central sealing projection 72 may serve to enhance secure sealing of the projection 72 with the tip 28 of the syringe barrel. It will, of course, be also appreciated that the dimensions of the sealing projection 72 may be chosen so that it will project into at least a portion of the passage 30 for blocking the passage and sealing the tip 28 (FIG. 12); to block tip 28 across the passage 30 without substantial insertion of projection 72 into passage 30 (FIG. 12A); or in various other manners as will be appreciated by those skilled in the art, so long as the projection 72 may close off the passage 30 to seal or cover the syringe tip.

As also seen in the Figures, an enclosure 110 may define a hemispherical-like structure surrounding the central projection 72 to accommodate the tip 28 when the cap 36 is in the closed position, as well as to guard against inadvertent touch contact with either the central sealing projection 72 when the cap 36 is in its open position, or with the syringe tip 28 when the cap is in its closed position. For instance, the dimensions of the various components, such as the length of the central sealing projection 72 or the depth of the enclosure 110, may be devised so that the tip of the sealing projection 72 remains recessed or otherwise disposed within the confines of the enclosure 110 so as not to extend beyond them. Thus, contamination of the supply of fluid which is in contact with the sealing projection 72 during use of the assembly is minimized. Inner surface 70 of roll cap 36 may also further include a slightly raised edge 79 on the inner surface 70 for sliding contact with guide walls 100, 101. In addition, spaced apart arrays of ribs 76 and 78 may be disposed on the edge 79 for frictionally engaging the guide walls 100, 101 to provide fictional resistance that prevents roll cap 36 from unintentionally sliding out of the open position shown in FIG. 11.

Roll cap 36 is further characterized by tapered edges 80 and 82 which respectively define a width "c" slightly less than the dimension "b" between the portions of side walls 46 and 48 defining channels 54 and 56. Additionally, the tapered thickness of roll cap 36, as measured in proximity to side edges 80 and 82, permits the sliding engagement of roll cap 36 in channels 54 and 56.

Roll cap 36 further includes an actuation tab 84 which is dimensioned to facilitate pushing and/or pulling of roll cap 36 relative to mounting collar 34. Actuation tab 84 includes locking undercuts 86 and 88 which are disposed and dimensioned to engage locking projections 62 and 64 for securely locking roll cap 36 in the closed condition as shown in FIGS. 12–14.

Cap assembly 12 is used by sliding tapered side edges 80 and 82 of cap 36 into channels 54 and 56 of collar 34 in a distal direction. The raised edge 79 formed along the inner surface 70 of the cap also slides along guide walls 100, 101 within the channels 54, 56 of collar 34. In this orientation, the orthogonally aligned surfaces of edge 79 against guide walls 100, 101 and between cap edges 80, 82 against side walls 46, 48 will substantially prevent separation of roll cap 36 from collar 34 in a proximal direction. However, further movement of cap 36 in a distal direction is enabled, as explained further below.

In this assembled condition, actuator tab 84 is radially outwardly of retaining walls 50 and 52, while side edges 80 and 82 are slidably engaged in channels 54 and 56. Additionally, portions of side edges 80 and 82 are disposed inwardly of guide projections 58 and 60.

The collar 34 with the cap 36 assembled therein can then be slid in a proximal direction over luer collar 32 of syringe barrel 14. As shown in FIG. 11, actuator tab 84 may be seated against the shoulder of syringe barrel 14 to further ensure that cap 36 cannot be moved proximally out of engagement with mounting collar 34 after cap assembly 12 is mounted to syringe barrel 14. Additionally, as shown in FIG. 11, cap 36 is disposed to prevent interference with interior regions of luer collar 32 and tip 30 so that syringe barrel 14 can be used easily. This illustrated alignment of cap 36 in collar 34 is maintained partly by the engagement of edge 79 and/or rib arrays 76 and 78 with the guide walls 100, 101 of the collar 34.

Cap 36 can be closed by exerting a distally directed force on actuator 84 with the thumb or forefinger of the hand holding syringe barrel 14. Actuator 84 will slide distally along the exterior of retaining walls 50 and 52. The tapered side edges 80 and 82 of cap 36 will slide through channels 54 and 56, with the edge 79 guided along the surface of guide walls 100, 101. As the cap 36 is projected still further distally along the axis of the mounting portion 38, a portion of cap 36 will strike and slide against, and pivot inwardly of, guide projections 58 and 60, to urge the cap 36 towards its closed position. The ramped portions 100a, 101a, disposed at generally acute angle θ and in sliding contact with the edge 79, allow clearance for, and further provide guidance for, the cap 36 to pivot as described above. The clearance gap "X" (FIG. 5) defined between guide projections 58 (60) and the end of ramped portions 101a (100a) provides sufficient space to allow the cap 36 to pivot about from its generally vertical, open orientation towards its generally horizontal, closed configuration, with the locking undercuts 86, 88 preventing the cap 36 from sliding out through the clearance gap "X" as it is closed. Thus, cap 36 will gradually rotate into the orientation shown in FIGS. 12–14 as it advances distally through channels 54 and 56.

In the fully closed position shown in FIGS. 12–14, sealing projection 72 of cap 36 will engage passage 30 of tip 28 of syringe barrel 14. Locking of cap 36 is achieved by engagement of portions of tab 84 defined by undercuts 86 and 88 of cap 36 with locking projections 62 and 64 on outwardly facing surfaces of retaining walls 50 and 52. Additionally, projections 58 and 60 will engage portions of the outer surface 68 adjacent side edges 80 and 82 of cap 36 to bias cap 36 into the sealed condition of FIGS. 12–14. As will be appreciated, in the closed orientation the locking projections 62, 64 exert an upward force on the undercuts 86, 88, with the projections 58, 60 exerting a downward force upon portions of the outer surface 68 of the cap 36. Hence, when locked into position, the cap is deflected so as to cause tip 28 of the syringe barrel 14 to exert a counterbalancing upward force into the central sealing projection 72 of the cap. Hence, cap 36 will be releasably snapped into secure locked engagement over the distal end of syringe barrel 14.

Cap 36 can be easily opened by merely exerting proximal forces on actuator 84 with the thumb or forefinger of the hand holding syringe barrel 14. These proximally directed forces 84 will cause undercuts 86 and 88 of cap 36 to disengage from locking projections 62 and 64 on collar 34, and will urge sealing projection 72 out of engagement with tip 28. Thus, cap 36 can be moved from the orientation depicted in FIGS. 12–14 back to the orientation shown in FIGS. 1 and 11.

As earlier explained, the cap assembly 12 may be readily adapted to numerous medical devices, wherein the cap assembly 12 may serve to seal a distal passageway of the device between successive uses. In most instances, the collar 34 of the cap assembly may be readily modified or otherwise appropriately configured to provide secure mounting to the device adjacent the passageway which is designed to be sealed. One example of such application is disclosed, for instance, in FIGS. 15–17. Here, cap assembly 12 has been modified for mounting to a stopcock assembly 120 associated with intravenous lines, catheters or the like. The stopcock assembly 120 generally features a female luer lock fitting 125 having a thread component 130. A lever arm 135 controls passage of fluids, medicaments or the like through the stopcock assembly 120 between an inlet port 136 and an outlet port 137. The female luer lock 125 is provided for selective attachment of syringes or the like utilized for injecting a medicine into the intravenous line controlled by the stopcock 120. The relative dimensions of the cap assembly 12 and, in particular, the collar 34 may be configured to enable the collar 34 to slide without interference in the space 136 defined between the bottom surface of stopcock lever 135 and the exterior of the female luer fitting 125 itself.

Figure 15:
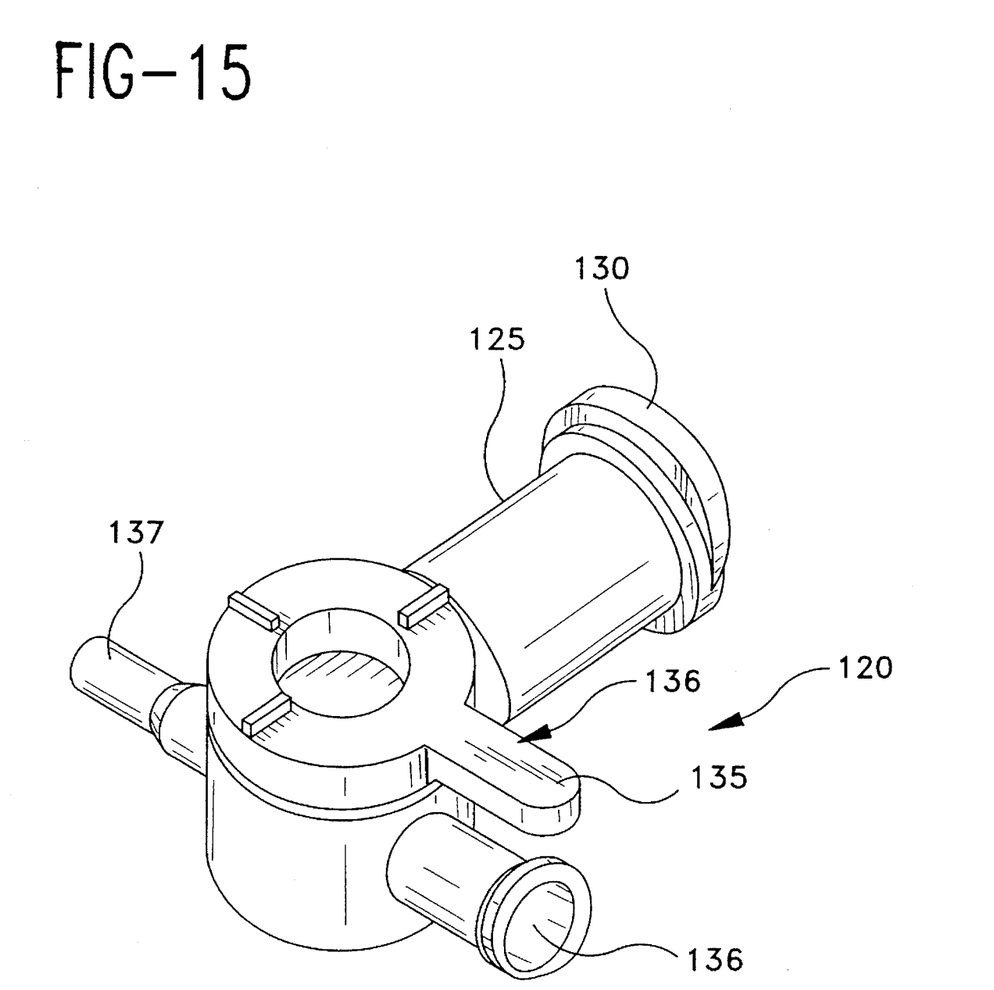
Figure 16:
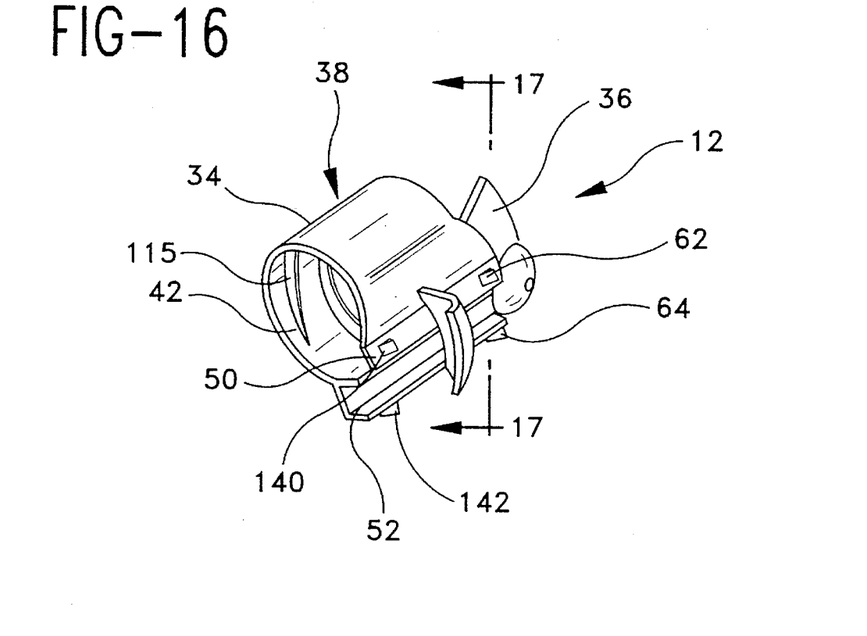
FIG. 16 is a perspective view of the roll cap assembly of the invention adapted for use with the female luer lock fitting of FIG. 15.

Here, the cap assembly 12 has been modified for fitting to the female luer lock 125. The collar 34 and, in particular, the circumferential surface 42 of the mounting portion 38 includes a mating thread component 115 for engagement with the thread 130 formed on the female luer lock 125. Thus, the cap assembly 12 may be screwed on to the stopcock assembly 120 so as to enable roll cap 36 to selectively seal a passageway formed in the female luer lock 125.

As earlier described an as seen in FIG. 17, the central sealing projection 72 of the roll cap 36 may include a conically tapered wall component 72a inclined, for instance, approximately 6° from the normal as defined by an axis 73 perpendicular to the cap 36. Of course, it will be understood that other acute angles may be chosen as need or desire dictate. The conically tapered configuration of the central sealing projection 72 serves to enhance and otherwise provide secure sealing of the projection 72 with the female luer lock 125 of stopcock 120.

Referring to FIG. 16, it will also be seen that to insure that the cap 36 will securely remain in its open position, a second pair of locking projections 140, 142 may be disposed at the proximal end of retaining walls 50, 52. The cap 36 can be slid downwards within the channels 54, 56 so that the locking undercuts 86, 88 slide over the locking projections 140, 142 and oriented beneath the locking projections so as to securely retain cap 36 in its open position. If desired, the locking projections 140, 142 as well as locking projections 62, 64 can be provided with ramped sections at either or both the proximal and distal ends of the locking projections to facilitate the ease with which the cap 36 may be displaced between its opened and closed positions. It will be understood and realized, of course, that the second set of locking projections 140, 142 and the ramped sections on either or both sets of projections can be employed with equal purpose in the embodiment described in FIGS. 1–14.

Figure 4A:
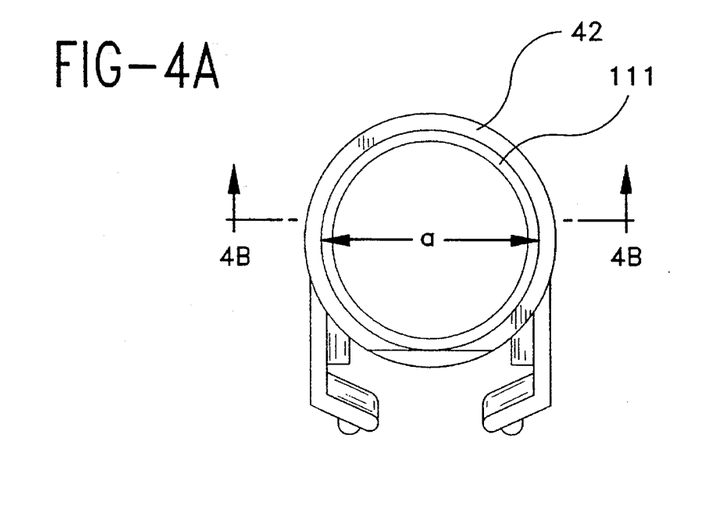
FIG. 4A depicts an alternate configuration of the collar, suitable for rotational mounting to a fitting.
Figure 4B:
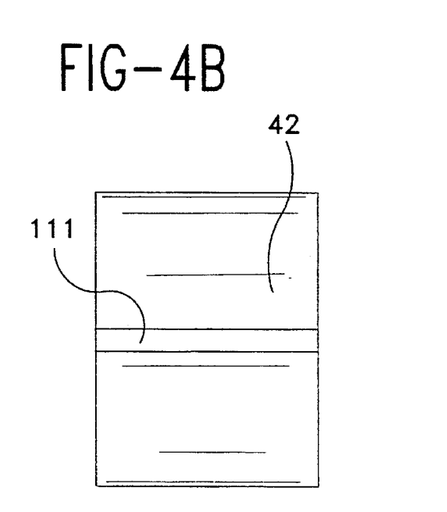
FIG. 4B is a frontal view of the configuration of FIG. 4A.
Figure 4C:
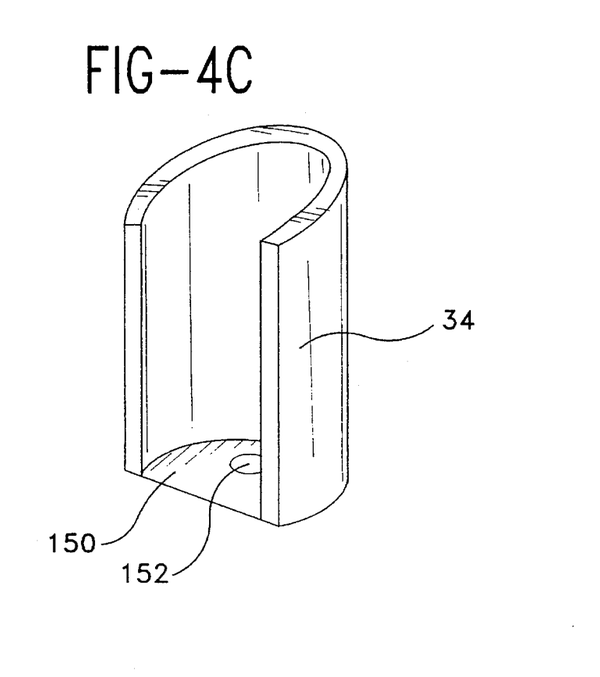
FIG. 4C illustrates another modification of the collar suitable for luer slip devices.
Figure 5:
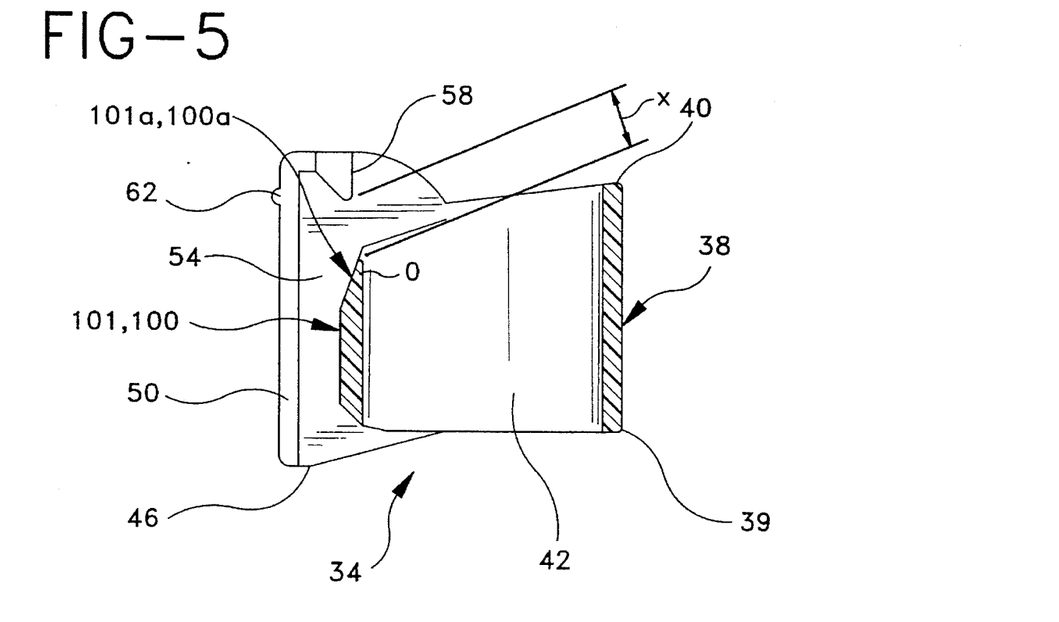
FIG. 5 is a cross-sectional view taken along line 5—5 in FIG. 4.
Figure 6:
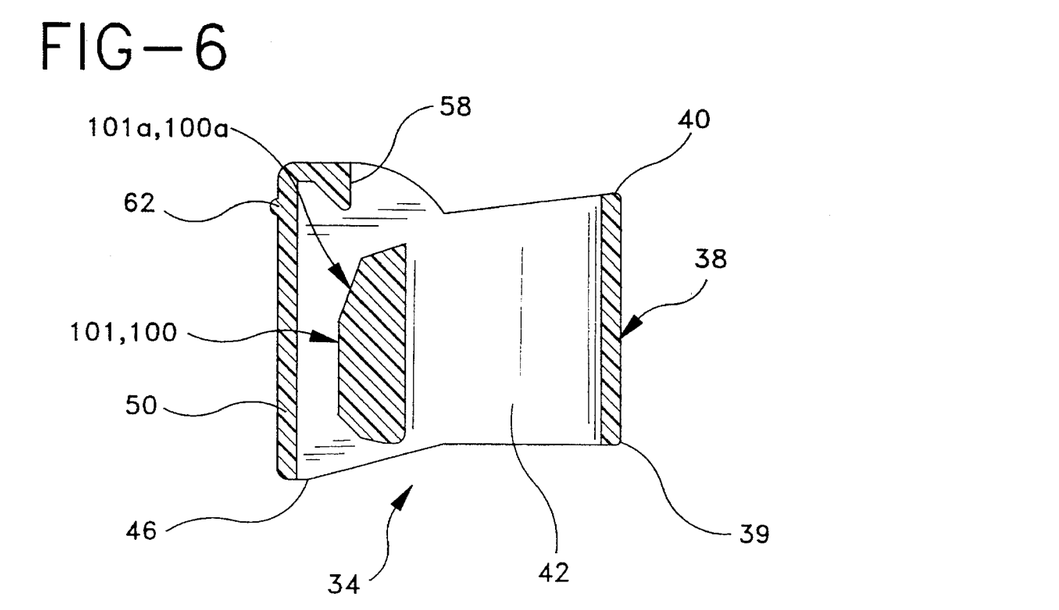
FIG. 6 is a cross-sectional view taken along line 6—6 in FIG. 4.
Figure 7:
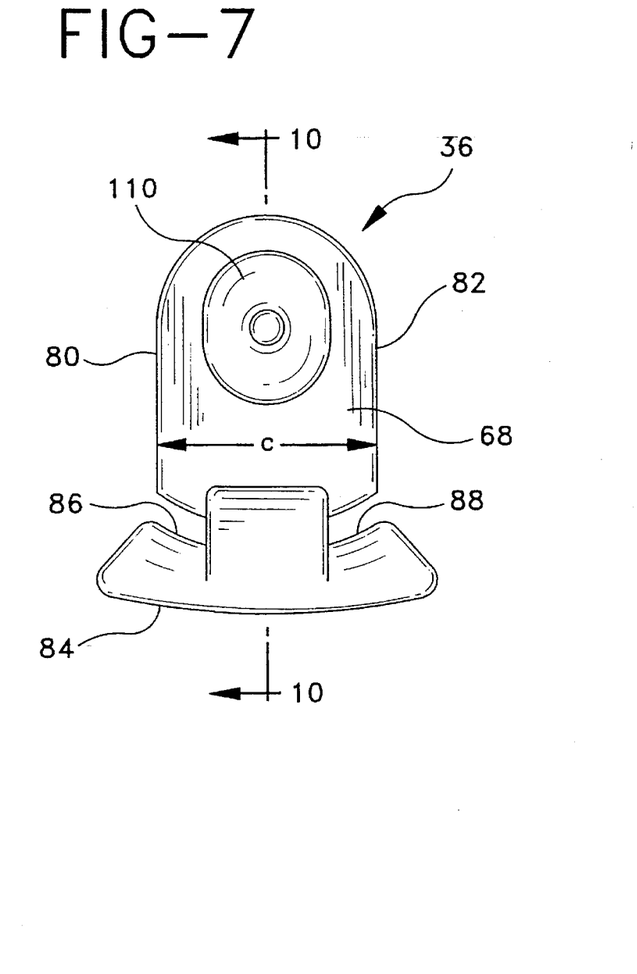
FIG. 7 is a top plan view of the cap for the roll cap assembly.
Figure 8:
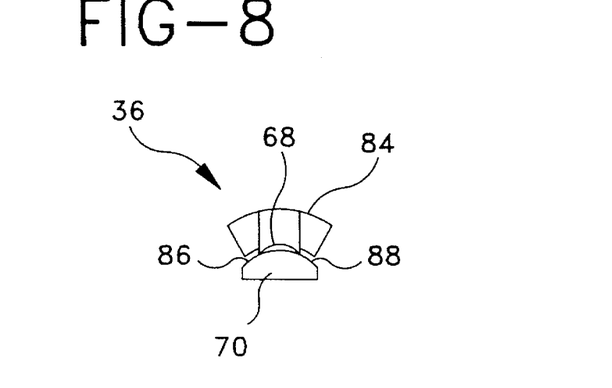
FIG. 8 is a frontal elevational view of the cap.
Figure 9:
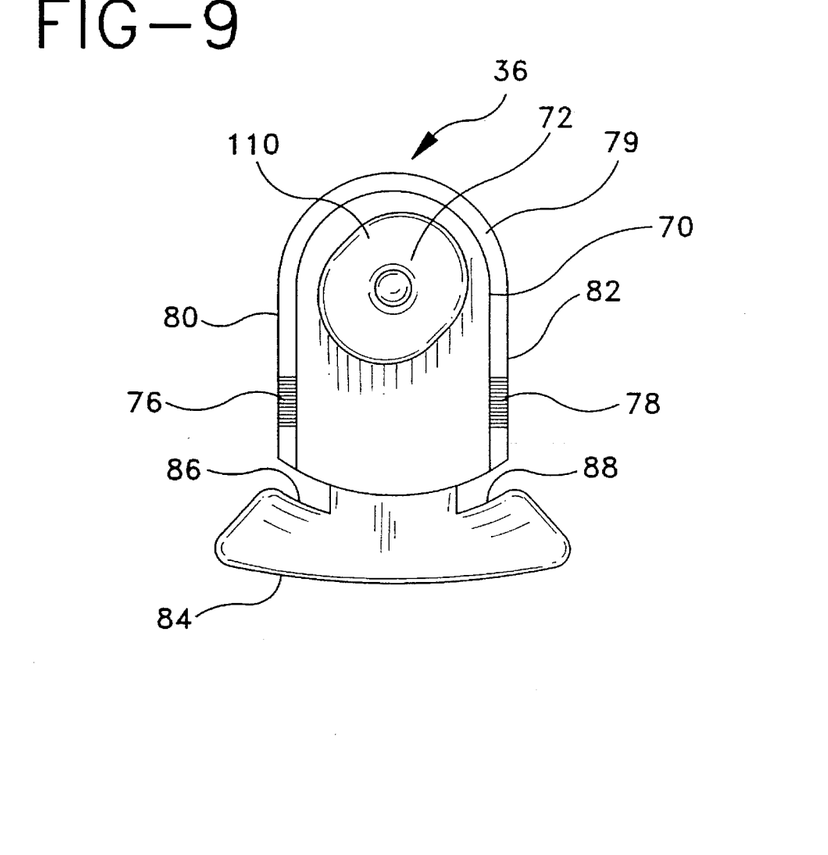
FIG. 9 is a bottom elevational view of the cap.

It will also be seen that the cap assembly 12 may be provided with the projection and groove arrangement described with respect to FIGS. 4a and 4b herein so as to enable the cap assembly 12 to be securely fixed but rotatable about the axis of female luer lock 125. This would be especially advantageous here in that the location of the cap 36 relative to the stopcock lever 135 may be displaced so that the two will not interfere during operation of either the stopcock lever 135 or the cap assembly 12. It will be further realized and appreciated by those skilled in the art that the modifications described with respect to stopcock assembly 120 are readily applicable to the syringe embodiment described in FIGS. 1–14.

Thus, it will be seen that the cap assembly herein described provides a convenient and ready way to selectively close or seal the passageways of numerous medical devices in current use. The roll cap assembly is readily modified to a variety of mountings or fittings, thereby enhancing the versatility of the device.

It will be understood and realized by those skilled in the art that various modifications may be made without departing from the spirit and scope of the appended claims, the invention not being limited to the specific embodiments shown.

What is claimed is:

1. In combination with a medical device having a passageway defining an axis, a protective cap assembly for selectively covering the passageway of said medical device, comprising:

a mounting fitting placeable on said medical device, said mounting fitting having opposed proximal and distal ends;

at least one side wall projecting transversely from said distal end of said mounting fitting;

a cap slidably and pivotally engaged with said side wall, said cap slidable along the sidewall in a direction parallel to the axis of the passageway between a first position where said cap is spaced from said passageway of said medical device and a second position where said cap is pivoted by a user to protectively cover said passageway.

2. The cap assembly of claim 1, wherein said medical device is a hypodermic syringe.

3. The cap assembly of claim 1, wherein said medical device is a stopcock.

4. The protective cap assembly of claim 3, wherein said cap assembly further comprises a threaded fitting for mating with a threaded female luer lock on said stopcock.

5. The cap assembly of claim 1, further comprising a sealing projection extending from said cap and dimensioned for sealing engagement with said passage of said medical device when said cap is in said second position.

6. The cap assembly of claim 5, wherein said sealing projection comprises a conically tapered wall component, said cap lying in a plane, said wall component inclined at an acute angle relative to a normal in the plane of said cap.

7. The cap assembly of claim 1, wherein said cap assembly is rotatably affixed to said medical device.

8. The protective cap assembly of claim 1, wherein said cap assembly is rotatably affixed to said medical device.

9. In combination with a hypodermic syringe defining an axis and having a passageway for fluid communication, a protective cap assembly for selectively covering the passageway of said hypodermic syringe, said syringe having an elongate barrel with opposed proximal and distal ends, comprising:

a mounting collar lockably engageable adjacent the distal end of the syringe barrel;

at least one side wall projecting transversely from said mounting collar; and a cap slidably and pivotally engaged with said side wall, said cap slidable in a direction parallel to the axis of the syringe between a first position where said cap is spaced from said passageway of said syringe and a second position where said cap is pivoted by a user to protectively cover said passageway.

10. The cap assembly of claim 9, further comprising means for preventing separation of said cap from said side wall.

11. The cap assembly of claim 10, further comprising means for releasably locking said cap in said second position.

12. The cap assembly of claim 9, further comprising a sealing projection extending from said cap, said sealing projection dimensioned for sealing engagement with said passage of said syringe when said cap is in said second position.

13. The protective cap assembly of claim 12, wherein said sealing projection is recessed within said cap.

14. The cap assembly of claim 9, wherein said at least one side wall comprises a pair of side walls, each of said pair of side walls projecting transversely from said mounting collar.

15. The cap assembly of claim 14, further comprising a retaining wall extending from each of said pair of side walls and defining a channel between said mounting portion of said collar and each of said retaining walls, said cap being slidably engaged in each of said channels.

16. The cap assembly of claim 15, wherein said cap comprises an actuator disposed externally of said channels and slidably engaged with said retaining walls for generating said sliding movement of said cap in said channels.

17. The cap assembly of claim 14, wherein said side walls are substantially parallel to one another.

18. In combination with a hypodermic syringe having an elongate barrel defining an axis and having opposed proximal and distal ends, a tip projecting longitudinally at said distal end having a passage therethrough and a luer collar concentrically surrounding said tip, a protective cap assembly for selectively covering the passage of said hypodermic syringe comprising:

a collar having a mounting portion configured for engagement around said luer collar of said syringe, and at least one side wall projecting from said mounting portion of said collar; and a cap slidably and pivotably engaged with said side wall of said collar, said cap slidable in a direction parallel to the axis of said syringe between a first position where said cap is spaced from said passage of said syringe and a second position wherein said cap is pivoted by a user to protectively cover said passage.

19. The protective cap assembly of claim 18, wherein said collar further comprises a retaining wall extending from portions of said at least one side wall, said retaining wall spaced from said mounting portion of said collar, said retaining wall defining a channel intermediate said retaining wall and said mounting portion of said collar, said cap being slidably and pivotably engaged within said channel.

20. The protective cap assembly of claim 19, wherein said collar includes opposed proximal and distal ends, said channel between said retaining wall and said mounting portion defining a first channel section, said collar further comprising at least one guide wall extending along portions of said side wall and said retaining wall, said guide wall comprising a ramped portion angularly aligned to said first channel section, said cap being slidably engaged with said guide projection for guiding said cap through said sliding and pivotable movement between said first and second positions of said cap.

21. The protective cap assembly of claim 19, wherein said cap includes an actuator slidably engaged with said retaining wall and disposed exteriorly of said channel for urging said cap between said first and second positions.

22. The protective cap assembly of claim 18, wherein said collar comprises locking means for releasably locking said cap in said second position.

23. The protective cap assembly of claim 22, wherein said locking means comprises at least one detent for releasable snapped engagement with portions of said cap.

24. The protective cap assembly of claim 18, wherein said cap includes a projection for sealing engagement with said passage in said syringe when said cap is in said second position.

25. In combination with a hypodermic syringe having an elongate barrel with opposed proximal and distal ends, a tip projecting longitudinally at said distal end having a passage therethrough, and a luer collar concentrically surrounding said tip, a protective cap assembly for selectively covering the passage of said syringe, comprising:

a collar having opposed proximal and distal ends configured for engagement around said luer collar of said syringe, said collar comprising at least one side wall and at least one retaining wall defining a channel, said side wall including a guide projection disposed adjacent the distal end of the collar;

at least one guide wall defined within the channel, said guide wall including a ramped portion oriented adjacent said distal end of the collar; and a cap for selectively sealing the tip of the hypodermic syringe, said cap comprising at least one tapered edge portion slidably engaged within the channel and a raised edge portion in sliding contact with the guide wall defined in the channel, said cap rotated into sealed engagement with the syringe tip as said raised edge portion is guided over the ramped portion of the guide wall and as a portion of said cap strikes said guide projection.

26. The protective cap assembly of claim 25, wherein said side wall comprises at least one locking projection on a side of said side wall opposite the channel, said cap further comprising an actuating tab disposed outside the channel and defining at least one undercut in opposed relation to the side wall, said undercut engaged by said locking projection to secure said cap in said sealed engagement with the tip of the syringe.

27. The protective cap assembly of claim 25, wherein said cap further comprises a sealing projection for engagement with the tip of the syringe, and an enclosure portion surrounding said sealing projection for preventing inadvertent touch contact with either of the syringe tip or sealing projection, said enclosure configured to accommodate said syringe tip when the cap is in a sealed condition.

28. The protective cap assembly of claim 27, wherein said tip is formed in a generally frusto-conical configuration and said enclosure is formed with at least a partially hemispherical portion.

* * * * *